(12) United States Patent
Batista

(10) Patent No.: US 10,986,870 B2
(45) Date of Patent: Apr. 27, 2021

(54) HANDHELD AEROSOL-GENERATING DEVICE AND CARTRIDGE FOR USE WITH SUCH A DEVICE

(71) Applicant: PHILIP MORRIS PRODUCTS S.A., Neuchatel (CH)

(72) Inventor: Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 443 days.

(21) Appl. No.: 15/526,934

(22) PCT Filed: Dec. 15, 2015

(86) PCT No.: PCT/EP2015/079804
§ 371 (c)(1),
(2) Date: May 15, 2017

(87) PCT Pub. No.: WO2016/096865
PCT Pub. Date: Jun. 23, 2016

(65) Prior Publication Data
US 2017/0325506 A1 Nov. 16, 2017

(30) Foreign Application Priority Data
Dec. 15, 2014 (EP) .................................. 14197851

(51) Int. Cl.
*A24F 47/00* (2020.01)
*A61M 15/06* (2006.01)
*A61M 16/00* (2006.01)

(52) U.S. Cl.
CPC .......... *A24F 47/008* (2013.01); *A61M 15/06* (2013.01); *A61M 2016/0039* (2013.01); *A61M 2205/3653* (2013.01); *H05B 2203/021* (2013.01)

(58) Field of Classification Search
None
See application file for complete search history.

(56) References Cited

U.S. PATENT DOCUMENTS

| 5,613,505 A | 3/1997 | Campbell |
| 5,894,841 A | 4/1999 | Voges |
| (Continued) | | |

FOREIGN PATENT DOCUMENTS

| CN | 102760921 | 10/2012 |
| CN | 202525085 U | 11/2012 |
| (Continued) | | |

OTHER PUBLICATIONS

International Search Report and Written Opinion for PCT/EP2015/079804 dated Mar. 9, 2016 (13 pages).

(Continued)

*Primary Examiner* — Michael H. Wilson
*Assistant Examiner* — Katherine A Will
(74) *Attorney, Agent, or Firm* — Mueting Raasch Group

(57) ABSTRACT

There is described a handheld aerosol-generating device which comprises an elongate tubular component having an axial length and which accommodates an electric power source. A mouthpiece portion having at least one air inlet and an outlet communicating with one another is detachably connected with the elongate tubular component. The electric power source is of an annular configuration extending at least about a major part of the axial length of the tubular component, and encloses an elongate receptacle which is open towards the mouthpiece portion, for accommodation of a cartridge comprising a supply of aerosol-forming substrate and an electrically operated vaporizer.

30 Claims, 4 Drawing Sheets

(56) References Cited

U.S. PATENT DOCUMENTS

| | | | | |
|---|---|---|---|---|
| 6,196,218 | B1* | 3/2001 | Voges | A24F 47/002 128/200.14 |
| 8,503,161 | B1* | 8/2013 | Chang | H01G 9/00 361/502 |
| 9,255,659 | B2 | 2/2016 | Cottard | |
| 9,675,108 | B2 | 6/2017 | Liu | |
| 2013/0192615 | A1 | 9/2013 | Scatterday | |
| 2013/0247924 | A1* | 9/2013 | Scatterday | A61M 15/06 131/329 |
| 2013/0255702 | A1* | 10/2013 | Griffith, Jr. | A24F 47/008 131/328 |
| 2014/0182609 | A1 | 7/2014 | Liu | |
| 2014/0182611 | A1 | 7/2014 | Liu | |
| 2015/0027459 | A1* | 1/2015 | Collett | A24F 47/008 131/328 |
| 2015/0291301 | A1* | 10/2015 | Cadieux | B65C 9/08 156/185 |

FOREIGN PATENT DOCUMENTS

| | | | |
|---|---|---|---|
| CN | 203182012 U | 9/2013 | |
| CN | 203219932 U | 10/2013 | |
| CN | 203646498 U | 6/2014 | |
| CN | 203748682 U | 8/2014 | |
| JP | 08-511175 | 11/1996 | |
| JP | H08-511966 | 12/1996 | |
| JP | 2013-545473 | 12/2013 | |
| WO | WO 2008/087161 | 7/2008 | |
| WO | WO-2015035510 A1 * | 3/2015 | A61M 15/06 |

OTHER PUBLICATIONS

Office Action issued in Japan for Application No. 2017-529374 dated Jan. 27, 2020 (8 pages). English translation included.

* cited by examiner

HANDHELD AEROSOL-GENERATING DEVICE AND CARTRIDGE FOR USE WITH SUCH A DEVICE

This application is a U.S. National Stage Application of International Application No. PCT/EP2015/079804, filed Dec. 15, 2015, which was published in English on Jun. 23, 2016, as International Publication No. WO 2016/096865 A1. International Application No. PCT/EP2015/079804 claims priority to European Application No. 14197851.0 filed Dec. 15, 2014.

The present invention relates to a handheld aerosol-generating device, such as an electrically operated smoking device. The invention further relates to a cartridge for use with a handheld aerosol-generating device.

From the prior art handheld aerosol-generating devices are known which basically comprise an elongate front component housing a power source, an intermediate component housing an electrically operated vaporizer and a mouth piece. Usually the mouthpiece comprises a cartridge with supply of aerosol-forming substrate. A control electronics including a puff sensor and a power management of the device may be part of the front component or of the intermediate component or even of the mouthpiece. Also, aerosol-generating systems are known which include a cartridge portion comprising both, a supply of aerosol-forming substrate and an electrically operated vaporizer. Such cartridge is sometimes referred to as a "cartomizer". The vaporizer typically comprises a coil of heater wire wound around an elongate wick soaked in liquid aerosol-forming substrate. The cartridge portion typically comprises not only the supply of aerosol-forming substrate and the electrically operated vaporizer, but also a mouthpiece, which the user may suck on in use, in order to draw aerosol into his mouth. For the purpose of this invention an aerosol-generating system comprises an aerosol-generating device and a cartridge comprising both, a supply of aerosol-forming substrate and an electrically operated vaporizer.

Current embodiments of handheld aerosol-generating systems existing in the market have dimensional proportions that do not cope with some market and customer requirements. Many of the known handheld aerosol-generating systems have a rather bulky configuration which does not meet the customers' expectations, in particular with regard to slimness, premium look, fashionable aesthetic and appeal, matching sophisticated and luxury environments. The known handheld aerosol-generating systems have diameters above 7.5 mm due to their technical approach, and involving the dimensions of known batteries, consumables/cartridges, electronic components and mouth pieces.

It is therefore and object of the invention to provide a novel configuration for a handheld aerosol-generating system, that will allow dimensions which meet the markets' and the customers' requirements.

According to one aspect of the invention a handheld aerosol-generating device is provided which comprises an elongate tubular component having an axial length and which accommodates an electric power source. A mouthpiece portion having at least one air inlet and an outlet communicating with one another is detachably connected with the elongate tubular component. The electric power source is of an annular configuration extending at least about a major part of the axial length of the tubular component, and encloses an elongate receptacle which is open towards the mouthpiece portion, for accommodation of a cartridge comprising a supply of aerosol-forming substrate and an electrically operated vaporizer.

The handheld aerosol-generating device according to the invention very much resembles a slim cigarette, known from the prior art. Contrary to conventional cigarettes the aerosol-generating system does not produce cigarette smoke, but rather an aerosol, which is commonly but actually inaccurately referred to as vapour. The aerosol is generated by heating an aerosol-forming substrate. The aerosol-forming substrate may be a liquid mixture of propylene glycol, glycerine and/or polyethylene glycol and concentrated or extracted flavourings. Optionally the aerosol-forming substrate may include a variable concentration of tobacco-derived nicotine. The provision of an electrical power source of annular configuration allows an elongate and slim build of the aerosol-generating device. Due to the annular construction of the electrical power source an elongate receptacle for a cartridge comprising a supply of aerosol-forming substrate and an electrically operated vaporizer is provided. This constructional feature limits the overall length of the aerosol-generating device, in spite of its slim configuration. In the assembled state the cartridge is located within the elongate receptacle and extends through the elongate tubular component towards the mouthpiece portion about concentrically with the surrounding electrical power source.

The electric power source may be one of a battery or an accumulator in a tubular metallic or polymeric configuration. In order to meet the power requirements of the aerosol-generating device, in particular of the electrically operated vaporizer, a battery or accumulator of high power density and capacity may be employed. In an embodiment of the handheld aerosol-generating device according to the invention the battery or accumulator may be constructed based on one of Lithium sulphur chemistry, or on hyper-capacitor chemistry elements. Examples of batteries or accumulators based on hyper-capacitor chemistry elements may comprise cobalt oxide in nanocarbon structures or nickel hydroxide in graphene/porous graphene structures. It should be noted that the electric power source may also be another form of charge storage device, such as, e.g. a capacitor. The electric power source may have a capacity that allows for the storage of enough energy for one or more smoking experiences; for example, the electric power source may have sufficient capacity to allow for the continuous generation of aerosol for a period of about six minutes, corresponding to the typical time taken to smoke a conventional cigarette, or for a period that is a multiple of six minutes. In another embodiment, the electric power source may have sufficient capacity to allow for a predetermined number of puffs or discrete activations of the electrically operated vaporizer.

The amount of electrical power provided to the aerosol-generating device that produces aerosol depends on a number of factors including the type of heating element used, the resistance of the heating element, the voltage of the battery, and the amperage produced by the battery. In turn, the voltage of the battery and the amperage produced by the battery depends on the geometry of the battery, the dimensions of the battery, and the battery chemistry (e.g., LiCo, LiFePo, lithium polymer chemistries). The electrical power available to the aerosol-generating device may be expressed in milliamp hours (mAh), which is total amount of power when the battery is charged. Electrical power for aerosol-generating devices may be between 90 mAh to 3000 mAh.

Determining the required dimensions of the major part of the axial length of the tubular component may be calculated based on the electrical power desired for the aerosol-generating device. If high power density and capacity batteries or accumulators based on hyper-capacitor chemistry elements, which may comprise cobalt oxide in nanocarbon structures or nickel hydroxide in graphene/porous graphene structures, are not used, the electrical power available to the aerosol-generating device will be confined by the dimensions available while maintaining the desired size of between 5 mm to 8 mm in diameter and 80 mm to 110 mm in length. Accordingly, the electrical power may be limited to between 15 mAh to 40 mAh. The term major part of the axial length of the tubular component as defined for the purpose of this invention includes a minimum length of 75% of the axial length of the tubular component and may extend of up to 100% thereof. The axial length of the tubular component for this purpose does not include that portion of the tube which is provided with connection elements to the mouthpiece portion.

In another embodiment of the handheld aerosol-generating device the elongate tubular component may be open on a front end opposite a longitudinal end thereof which faces toward the mouth piece. The annular electrical power source, e.g. a battery or an accumulator of annular configuration, may be provided with two electrical recharging contacts which are located near the front end of the elongate tubular component. The electrical recharging contacts are provided such that they face the elongate receptacle for the cartridge. They may, e.g. be constructed as spring loaded metallic levers or as metallic spring clips. When the cartridge is removed a two terminal mini jack may be inserted into the front end of the elongate tubular component to provide electrical contact with the two electrical recharging contacts. The two terminal mini jack may, e.g. be constructed similar to a mini jack commonly used for headphones or the like. With this construction a recharging of the annular electrical power source may be accomplished without any disassembly of the aerosol-generating device. The open front end of the elongate tubular component also allows an insertion of the cartridge from the front end thereof. Thus, the cartridge comprising a supply of aerosol-forming substrate and an electrically operated vaporizer may be inserted into the aerosol-generating device without any disassembly thereof. Constructional features such as, e.g., a cap on a trailing end of the cartridge may be provided, in order to ascertain that the cartridge is inserted correctly, with the end bearing the electrically operated vaporizer entering the receptacle in the elongate tubular component first. The cap on the trailing end of the cartridge may e.g. have different colours, in order to allow an identification of the specific content of the cartridge and its branding.

In yet another embodiment of the invention the length of the cartridge may be selected such, that when it is completely inserted into the elongate tubular component, its trailing end does not extend from the tubular component. Thus, an accidental breakage of a protruding portion of the cartridge may be avoided.

The elongate tubular component and the mouthpiece may be directly detachably connected with one another. The connection may e.g. be a threaded connection or a bayonet joint. In another embodiment of the handheld aerosol-generating device according to the invention the elongate tubular component and the mouthpiece portion may be detachably connected by a tubular coupling member, which is arranged in between the two components. The tubular coupling member may be provided with corresponding threads to enable a detachable connection with the elongate tubular component and the mouthpiece part, respectively. The tubular coupling member may comprise mechanical locking elements for releasably securing the cartridge and mechanical contacts for establishing an electrical connection with the electrically operated vaporizer on the cartridge. The mechanical locking elements for releasably securing an inserted cartridge may be of the push lock/release type and may comprise a spring and a coupling element. When a cartridge is inserted into the elongate receptacle of the elongate tubular component its leading end bearing the electrically operated vaporizer pushes against the mechanical locking elements and thus the cartridge is releasably locked. By pushing the cartridge towards the mouthpiece part the mechanical locking mechanism is activated again and the cartridge is released. In case that the elongate tubular component is directly connected with the mouthpiece part the mechanical locking elements for releasably securing the cartridge and the mechanical contacts for establishing an electrical connection with the electrically operated vaporizer on the cartridge may be provided in the mouth piece part.

Alternatively, the locking mechanism may comprise at least one O-ring or other retention medium that is appropriately dimensioned to grip the walls of the cartridge frictionally when inserted. The O-ring may e.g. be arranged within the mouthpiece portion or the tubular coupling member. The user can then insert or remove the cartridge by pushing the cartridge into the device such that the walls are gripped by the retention medium and pull the cartridge to remove it from the device. Use of a retention medium has the additional benefit of acting as a leakage prevention means and retaining the liquid during use. In order for the cartridge to be easier pulled out again, a small portion of the trailing end of the cartridge may protrude from the elongate tubular component. This small portion may be long enough to be gripped by the fingers of the user, but short enough to prevent any accidental damage to the cartridge. The protruding portion of the cartridge may, e.g., be an LED which is attached to the trailing end of the cartridge. The outer diameter of the protruding portion of the cartridge, which e.g. may bear an LED, may correspond to the outer diameter of the elongate tubular component. This reduces the danger of an accidental breakage of the cartridge due to shearing forces and contributes to the homogeneous look of the handheld aerosol-generating device.

The appropriation of a tubular coupling member for detachably connecting the elongate tubular component and the mouthpiece portion of the handheld aerosol-generating device may constitute a separate aspect of the invention or it may be provided in combination with the aforementioned and described embodiments of the aerosol-generating device.

In a still further embodiment of the handheld aerosol-generating device the electric power source may be provided with first electrical contacts which are located near the front end of the elongate tubular component and facing the elongate receptacle for the cartridge for interaction with corresponding second electrical contacts near a trailing end portion of the cartridge which may be received in the elongate receptacle. The second electrical contacts may be electrically connected with an LED which is attached to the trailing end of the cartridge. The second electrical contacts may be configured as metallic jackets around the cartridge. The first electrical contacts on the electrical power source may e.g. be identical with the recharging contacts or they may be separate contacts. They may, e.g. be constructed as spring loaded metallic levers or as metallic spring clips.

The handheld aerosol-generating device may further comprise a control electronics including a puff sensor and a power management of the device. The control electronics is connected to the electrical power source and capable of making electrical contact with the electrically operated vaporizer as the cartridge is inserted into the aerosol-generating device. The control electronics may be configured to monitor the electrical resistance of the vaporizer, and to control the supply of power to the vaporizer dependent on detected electrical resistance of the vaporizer. The control electronics may comprise a microprocessor, which may be a programmable microprocessor. The control electronics may be configured to regulate the supply of power to the vaporizer. Electric power may be supplied to the vaporizer continuously following activation of the system or it may be supplied intermittently, such as on a puff-by-puff basis, depending on the signals of the puff sensor. The control electronics may be provided on one of the elongate tubular component, the mouthpiece portion, and, if applicable the tubular coupling member. In order to cope with the slim build of the handheld aerosol-generating device the control electronics may be provided as printed circuitry on polymeric film.

The elongate tubular component and the tubular coupling member of the handheld aerosol-generating device may be made of a rigid material. As used herein "rigid" means that the elongate tubular component and the tubular coupling member are self-supporting. The rigid material may be selected from metals, alloys, plastics, or composite materials containing one or more of those materials, or thermoplastics that are suitable for food or pharmaceutic applications, such as, e.g., PET, HDPE, PP, PEEK, PS, PVC, PEN, copolymers of the mentioned plastics, bio-plastics, such as, e.g., PLA or PEF, filled plastics and mixtures of the mentioned plastics. Preferably the material is light and non-brittle. These materials have the required rigidity and are of relatively small weight such, that the comfort of the user is not impaired. The mentioned thermoplastics materials are easy to manufacture e.g. in an injection moulding process.

In yet another embodiment of the handheld aerosol-generating device the elongate tubular component, the tubular coupling member, if applicable, and the mouthpiece portion may be enclosed with a flexible casing. The casing provides a mechanical and a permeable barrier. In an embodiment of the invention the flexible casing of the handheld aerosol-generating device is made of a laminated auto-adhesive paper foil. The paper foil gives the soft touch and may be designed to give the handheld aerosol-generating device a finishing similar to that of slim cigarettes known from the prior art.

While known aerosol-generating systems or "personal vaporizers" of the prior art have relatively large outside diameters, the handheld aerosol-generating device according to the invention may be configured such that it's outside diameter is amounts to from 5 mm to 8 mm. In yet another embodiment of the handheld aerosol-generating device the outside diameter may be only from 4 mm to 6 mm. Together with a total axial length of from 80 mm to 110 mm the handheld aerosol-generating device according to the invention is a very slim and light device. Its appearance is very elegant and appealing, and matches the customers' requirement for a sophisticated premium product. The elongate tubular component may have an axial length which amounts to from 65 mm to 81 mm. The elongate receptacle within the elongate tubular component may have a diameter of from 2 mm to 2.6 mm. The diameter of the elongate receptacle corresponds to an internal diameter of the elongate tubular component. The tubular coupling member may have an axial length which amounts to from 4 mm to 9 mm. The mouthpiece portion may have an axial length which amounts to from 11 mm to 20 mm. In case that the handheld aerosol-generating device comprises only an elongate tubular member and a mouthpiece portion, the axial length of the mouthpiece portion will include that of the tubular coupling member, resulting in the specified total length of the handheld aerosol-generating device of from 80 mm to 110 mm.

According to another aspect of the invention a cartridge for use in an electrically operated aerosol-generating device in accordance with the invention is provided which comprises a tubular container for holding a liquid aerosol-forming substrate, the tubular container having an opening; an elongate, cylindrical wick having a first longitudinal section which extends into the container, and a second longitudinal section which extends axially beyond the opening of the container; an electrically operated vaporizer which is located at the second longitudinal section of the wick. The cartridge may be refillable. For that purpose the wick may be tightly and detachably secured within the opening of the tubular container. After removal of the wick from the tubular container the refilling may be accomplished, e.g. with use of a syringe which may be introduce through the opening of the tubular container. After the refilling the wick may be secured in the opening of the tubular container again, with the first longitudinal section extending into the container and the second longitudinal section protruding from the opening. E.g. the wick may protrude through a plug which may be sealingly and detachably inserted into the opening of the tubular container.

The slim configuration of the handheld aerosol-generating device according to the invention necessitates a likewise slim design of the cartridge which is configured to fit into the aerosol-generating device. The wick constantly transports an amount of the liquid aerosol-forming substrate to the electrically operated vaporizer, which produces the aerosol. The electrically operated vaporizer in the inserted position is located such, that air flowing from the at least one air inlet towards the outlet of the mouthpiece portion travels about transversal around the wick during puffing, and about longitudinally towards the mouth of the consumer. The air travelling about transversal around the wick takes up the aerosol which is produced by the electrically operated vaporizer during puffing. Usually the mouthpiece portion is provided with a plurality of air inlets in order to provide the required magnitude of air flow. The longitudinal air path inside of the mouthpiece portion may have the shape of a jet nozzle, similar to that of a Lavale nozzle. Due to this shape the air flow including the aerosol which is produced by the electrically operated vaporizer on the wick is accelerated just prior to entry into the mouth of the consumer.

In an exemplary embodiment of the invention the electrically operated vaporizer may comprise an electrical coil which is wound at least around a part of the second longitudinal section of the wick, the electrical coil having two ends which are connected with two electrical contacts that are located on the second longitudinal section of the wick, closer to the opening of the container than the electrical coil. When inserted into the aerosol-generating device the electrical contacts on the wick automatically make contact with corresponding electrical contacts in the mouthpiece or the tubular coupling member.

The two electrical contacts on the wick may be two metallic jackets which are disposed about the second longitudinal section of the wick and which are electrically separated and isolated from each other by an intermediate polymeric jacket. This configuration of the electrical contacts does not require a specific rotational position of the cartridge as it is inserted into the aerosol-generating device. The metallic jackets extend 360° around the wick and automatically make contact to the corresponding contacts within the mouthpiece portion or, if applicable, the tubular coupling member, regardless of the rotational orientation of the cartridge. The two corresponding electrical contacts within the mouthpiece portion or the tubular coupling member, which are connected with the electrical power source, may e.g. be constructed as spring loaded metallic levers or as metallic spring clips. Upon insertion of the cartridge into the aerosol-generating device automatically an electrical contact between the two electrical contacts on the wick with the two corresponding contacts within the mouthpiece portion or the tubular coupling member is made.

In another embodiment of the invention the electrical coil of the electrically operated vaporizer may be a resistance heating coil. The electrical coil may be made from stainless steel which is practically inert with regard to the produced aerosol.

In yet another embodiment of the cartridge the electrical coil may be an induction coil. In this embodiment of the cartridge the second longitudinal section of the wick, at least within the longitudinal extension of the induction coil comprises a susceptor material. The induction coil is capable of generating an alternating electromagnetic field from an AC source such as an LC circuit. Heat generating eddy currents are produced in the susceptor material. The susceptor material is in thermal proximity of the aerosol forming substrate which is transported by the wick. The heated susceptor material in turn heats the second longitudinal end of the wick which comprises the aerosol forming substrate which is capable of releasing volatile compounds that can form the aerosol.

In another embodiment of the cartridge the susceptor material may be one of particulate, or filament, or mesh-like configuration, or mixtures thereof. E.g., a configuration of the susceptor material may be chosen, which presents a large surface area to the wick containing the aerosol-forming substrate which is capable of releasing volatile compounds that can form an aerosol, in order to enhance the heat transfer. Thus, e.g., the susceptor material may be of particulate configuration. The particles preferably may have an equivalent spherical diameter of 10 µm-100 µm and may be distributed throughout the second longitudinal section of the wick at least within the longitudinal extension of the induction coil. The equivalent spherical diameter is used in combination with particles of irregular shape and is defined as the diameter of a sphere of equivalent volume. At the selected sizes the particles may be distributed throughout the second longitudinal section of the wick as required and they may be securely retained therein. In a further embodiment the susceptor material may be of a filament configuration. Filament structures may have advantages with regard to their manufacture, and their geometrical regularity and reproducibility. In still another embodiment of the cartridge the susceptor material may be of a mesh-like configuration which e.g. may at least partially form an encasement of the second longitudinal section of the wick. The term "mesh-like configuration" includes layers having discontinuities there through. For example the layer may be a screen, a mesh, a grating or a perforated foil.

In yet another embodiment of the cartridge the second longitudinal section of the wick only contains suceptor material of the afore-mentioned kinds of configuration. In this embodiment the induction coil is not located on the second longitudinal section of the wick. Rather it may be integrated within the mouthpiece portion or within the tubular coupling member of the aerosol-generating device. When the cartridge is inserted into the aerosol-generating device, the second longitudinal section of the wick, which comprises the susceptor material, is located within the induction coil, and heating thereof for the production of aerosol may be accomplished. The induction coil is capable of generating an alternating electromagnetic field from an AC source such as an LC circuit. Heat generating eddy currents are produced in the susceptor material. The susceptor material is in thermal proximity of the aerosol forming substrate which is transported by the wick. The heated susceptor material in turn heats the second longitudinal end of the wick which comprises the aerosol forming substrate which is capable of releasing volatile compounds that can form the aerosol.

Due to the fact that the cartridge is supported within the elongate recess in the elongate tubular component the tubular container may even have certain flexibility. This increases the choice of materials the tubular container may be made from.

In yet another embodiment of the cartridge the tubular container at a longitudinal end portion opposite the opening may be provided with two electrical contacts which are electrically connected with a LED which may be attached to the longitudinal end of the container opposite the opening. The LED may be activated as long as a customer sucks on the mouthpiece portion, thus copying the glowing tip of a cigarette. Depending on the contents of the aerosol forming substrate the LED may have a different colour.

The cylindrical wick protruding from the tubular container of the cartridge may be made of a capillary material. The capillary material may have a fibrous or spongy structure. The capillary material may comprise a bundle of capillaries. For example, the capillary material may comprise a plurality of fibres or threads or other fine bore tubes. The structure of the capillary material forms a plurality of small bores or tubes, through which the liquid may be transported by capillary action. Examples of suitable capillary materials are sponge or foam material, ceramic- or graphite-based materials in the form of fibres, foamed metal or plastics material, fibrous material, for example made of spun or extruded fibres, such as, cellulose acetate, polyester, or bonded polyolefin, polyethylene, terylene or polypropylene fibres, nylon fibres of ceramic. The capillary material may have any suitable capillarity and porosity so as to be used with different liquid physical properties, including but not limited to viscosity, surface tension, density, thermal conductivity, boiling point and vapour pressure, which allow the liquid to be transported through the capillary material by capillary action.

The afore-described embodiments of the handheld aerosol-generating device and of suitable cartridges will become more apparent from the following detailed description, reference being made to the accompanying schematic drawings which are not to scale, in which.

In the schematic drawings of embodiments of a handheld aerosol-generating device for the purpose of simplification like elements and components bear the same reference numerals.

Figure 1:
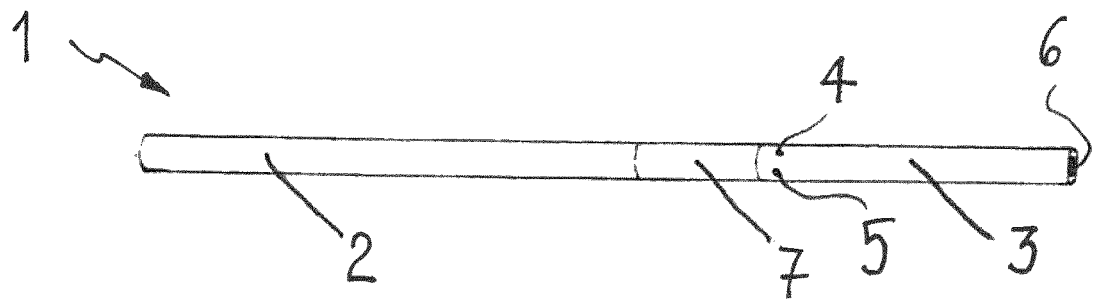
FIG. 1 shows an embodiment of an aerosol-generating device according to the invention.

A first embodiment of a handheld aerosol-generating device, which is depicted in FIG. 1, is generally designated with reference numeral 1. It comprises an elongate tubular component 2, which accommodates an electrical power source, and a mouthpiece portion 3, which is provided with at least one, preferably with a plurality of air inlets 4, 5 and an outlet 6, which communicate with one another. The mouthpiece portion 3 is the end of the aerosol-generating device on which the consumer will suck, in order to draw an aerosol of his choice into his mouth. A tubular coupling member 7 is arranged in between the elongate tubular component 2 and the mouthpiece portion 3 and detachably combines the two parts. The elongate tubular component 2 has an axial length which amounts to from 65 mm to 81 mm. The tubular coupling member 7 has an axial length which amounts to from 4 mm to 9 mm. The mouthpiece portion 3 has an axial length of from 11 mm to 20 mm. A total length of the handheld aerosol-generating device 1 amounts to from 80 mm to 110 mm. The handheld aerosol-generating device 1 has an outer diameter which amounts to from 5 mm to 8 mm.

Figure 2:
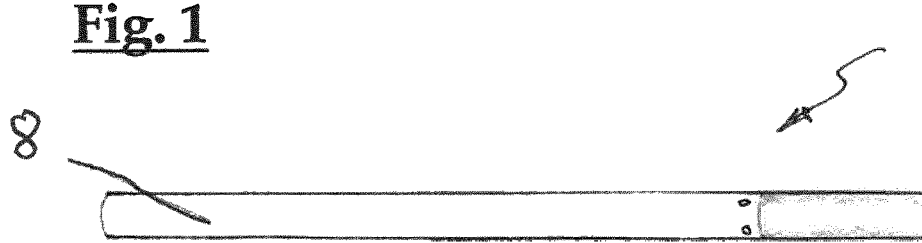
FIG. 2 shows another embodiment of the aerosol-generating device.

FIG. 2 shows a variant of an aerosol-generating device, which again generally bears reference numeral 1. As shown the aerosol-generating device comprises a casing 8, which may e.g. be a laminated paper foil which is wrapped about the individual components of the aerosol-generating device. The casing 8 gives the aerosol-generating device 1 a soft touch and an appearance of an elegant slim cigarette.

Figure 3:
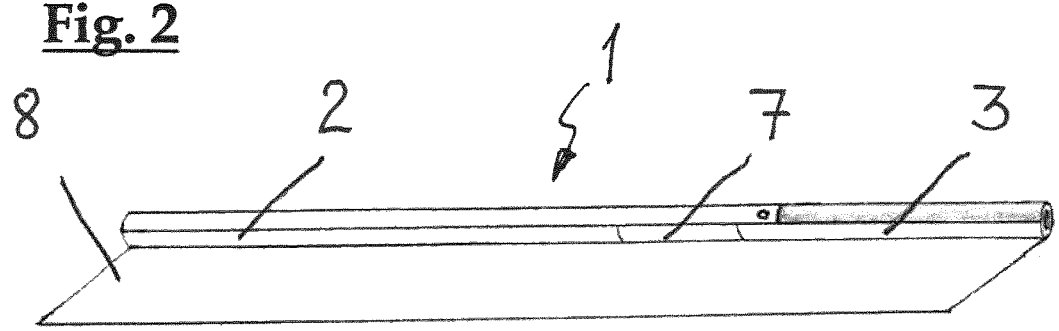
FIG. 3 shows the aerosol-generating device of FIG. 2 in a partly "disassembled" state.

FIG. 3 shows the aerosol-generating device 1 in a state, in which an auto adhesive laminated paper-foil 8 is being wrapped about the components of the device 1, namely the elongate tubular component 2, the tubular coupling member 7, and the mouthpiece portion 3. The paper foil not only gives the aerosol-generating device the soft touch and elegant appearance, but it also provides a mechanical protection and a permeable barrier.

Figure 4:
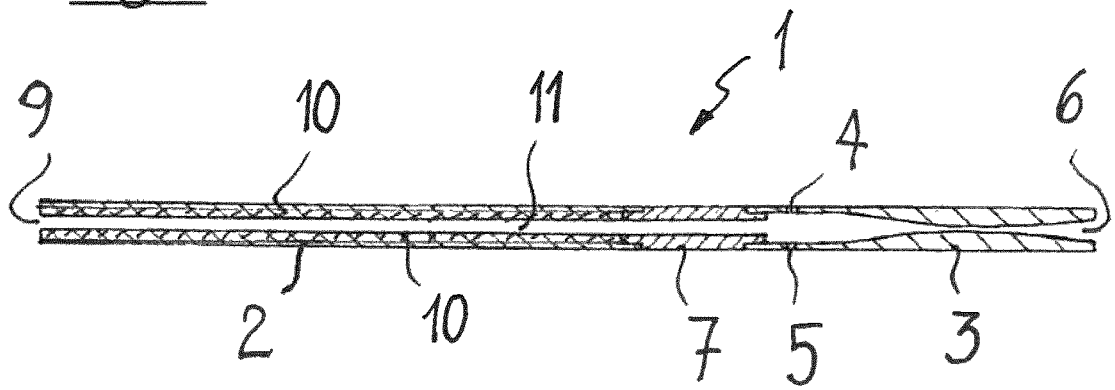
FIG. 4 shows an axially sectioned view of an aerosol-generating device.

In FIG. 4 the embodiment of the aerosol-generating device 1 of FIG. 1 is shown in an axially sectioned view. The elongate tubular component 2, the tubular coupling member 7, and the mouthpiece portion 3 are detachably connected with one another. The air inlets 4, 5 and the outlet 6 are shown in the drawing. The detachable connection in between the elongate tubular component 2 and the tubular coupling member 7, and the detachable connection in between the tubular coupling member 7 and the mouthpiece portion 3 may e.g. be a threaded connection or a bayonet joint, respectively. As can be seen in FIG. 4, the elongate tubular component 2 may have an opening 9 on a longitudinal front end opposite a longitudinal rear end facing toward the tubular coupling member 7 and the mouthpiece portion 3. On the inside of the elongate tubular component 2 there is arranged an electric power source 10. The electric power source 10 extends along 75% to about the entire length of the elongate tubular component 2 and is of an annular configuration. The electric power source 10 may be a battery or an accumulator in a tubular metallic or polymeric configuration, or it may be another form of charge storage device, such as, e.g. a capacitor. Due to the annular configuration of the electric power source 10 an elongate receptacle 11 is formed, which is open towards the coupling member 7 and the mouthpiece portion 3. The elongate receptacle 11 is adapted for accommodation of a cartridge comprising a supply of aerosol-forming substrate and an electrically operated vaporizer. Depending mainly on the cross-section of the aerosol-generating device 1, the elongate receptacle 11 may be of a cylindrical shape and may have an about circular cross-section. An internal diameter of the elongate receptacle 11 amounts to from 2 mm to 2.6 mm. The handheld aerosol-generating device 1 may further comprise a control electronics (not shown) including a puff sensor and a power management of the device. The control electronics may be provided on one of the elongate tubular component 2, the mouthpiece portion 3, and the tubular coupling member 7. In order to cope with the slim build of the handheld aerosol-generating device 1 the control electronics may be provided as printed circuitry on polymeric film.

Figure 5:
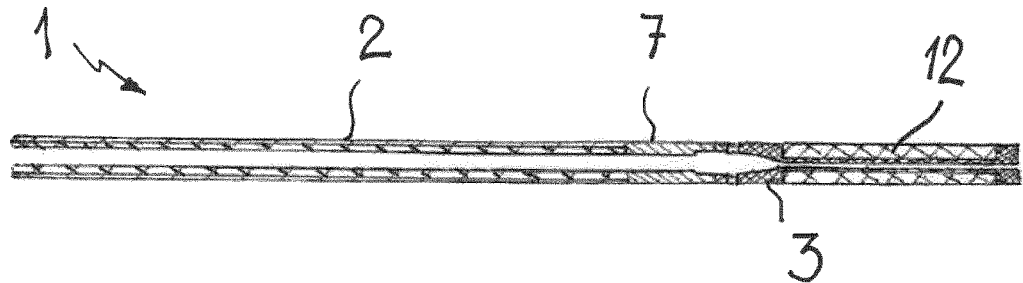
FIG. 5 shows an axially sectioned view of variant embodiment of the aerosol-generating device.

In the embodiment of the aerosol-generating device 1 which is shown in FIG. 5, a control-electronics 12 in the shape of a printed circuitry on polymeric film is integrated in the mouthpiece portion 3. This embodiment of the aerosol-generating device 1 may then be provided with a casing 8 (FIG. 2), which may e.g. be a laminated paper foil which is wrapped about the individual components of the aerosol-generating device 1, namely the elongate tubular member 2, the tubular coupling member 7 and the mouthpiece 3. The casing 8 then provides a mechanical protection for the control electronics 12.

Figure 6:
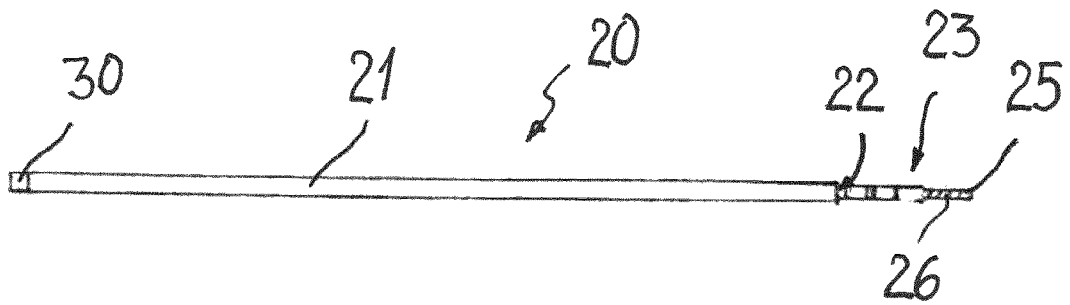
FIG. 6 shows a cartridge for use in combination with an aerosol-generating device according to the invention.

In FIG. 6 a cartridge 20 for insertion into a handheld aerosol-generating device is shown. The cartridge 20 comprises a tubular container 21 for holding a liquid aerosol-forming substrate. The tubular container 21 at one longitudinal end has an opening 22, from which a second longitudinal section 25 of an elongate, about cylindrical wick 23 protrudes. The second longitudinal section 25 of the wick 23 bears an electrically operated vaporizer, which comprises an electric coil 26. At a longitudinal end portion opposite the opening 22 the cartridge may be provided with two electrical contacts which are electrically connected with a light emitting diode (LED) 30.

Figure 7:
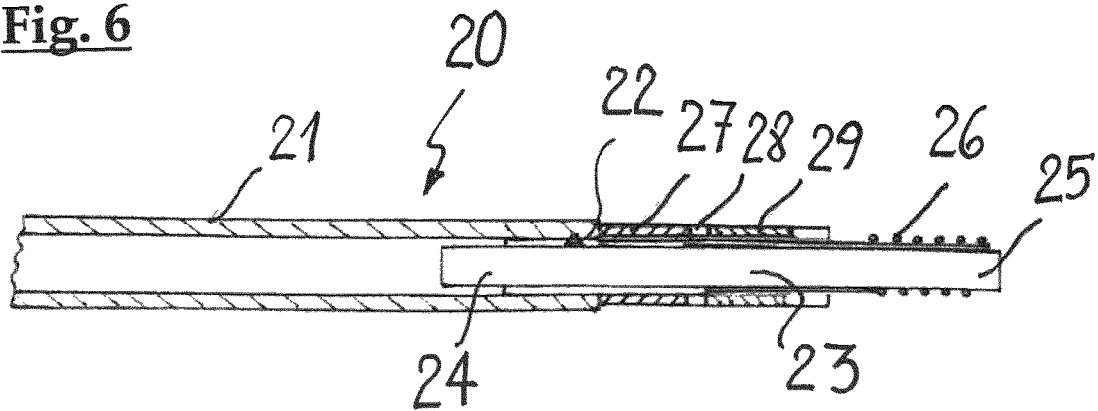
FIG. 7 shows an axially sectioned view of an end portion of the cartridge bearing an electrically operated vaporizer.

FIG. 7 shows a cross-sectional view of the part of the cartridge 20 which comprises the wick 23. The wick 23 comprises a first longitudinal section 24 which extends into the container 21. There it is in contact with a usually liquid aerosol-forming substrate. The second longitudinal section 25 of the wick 23 extends axially beyond the opening 22 of the container 21. The electrically operated vaporizer comprises an electrical coil 26 of a resistance heating which is wound at least around a part of the second section 25 of the wick 23. The electrical coil 26 may be made from stainless steel and has two ends which are connected with two electrical contacts 27, 29 that are located on the second section 25 of the wick 23, closer to the opening 22 of the container 21 than the electrical coil 26. The two electrical contacts 27, 29 on second longitudinal section 25 of the wick 23 may be two metallic jackets which are disposed about the second section of the wick and which are electrically separated and isolated from each other by an intermediate polymeric jacket 28. This configuration of the electrical contacts does not require a specific rotational position of the cartridge 20 when it is inserted into the aerosol-generating device. The metallic jackets extend 360° around the wick 23 and automatically make contact to two corresponding contacts, which are connected with the electric power source and may e.g. be located within tubular coupling member 7 (FIG. 5) regardless of the rotational orientation of the cartridge 20. The two corresponding electrical contacts within the tubular coupling member may e.g. be constructed as spring loaded metallic levers or as metallic spring clips. Upon insertion of the cartridge 20 into the aerosol-generating device 1 automatically an electrical contact between the two electrical contacts 27, 29 on the wick 23 with the two corresponding contacts within the tubular coupling member is made. The slim configuration of the handheld aerosol-generating device according to the invention necessitates a likewise slim design of the cartridge 20 which is configured to fit into the elongate receptacle 11 in the elongate tubular component 2 (FIG. 4).

Figure 13:
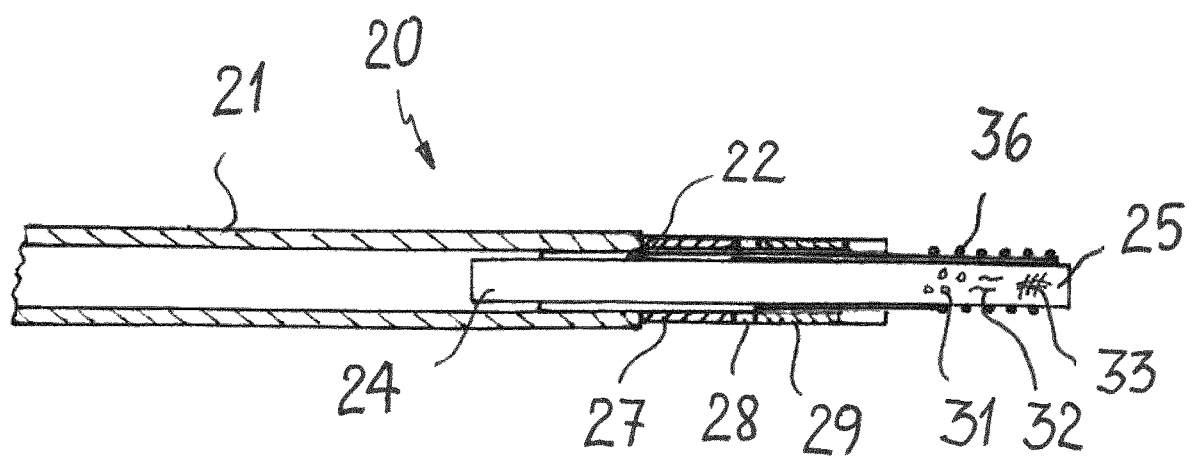
FIG. 13 shows an axially sectioned view similar to FIG. 7 of an end portion of the cartridge bearing an electrically operated vaporizer comprising susceptor material and an induction coil.

In FIG. 13 a view of the cartridge is shown which is very similar to that of FIG. 7. The cartridge again is generally designated with reference numeral 20. The wick 23 comprises again a first longitudinal section 24 which extends into the container 21. There it is in contact with a usually liquid aerosol-forming substrate. The second longitudinal section 25 of the wick 23 extends axially beyond the opening 22 of the container 21. The electrically operated vaporizer comprises an induction coil, which is designated with reference numeral 36. The induction coil 36 is wound at least around a part of the second longitudinal section 25 of the wick 23. The induction coil 36 has two ends which are connected with two electrical contacts 27, 29 that are located on the second section 25 of the wick 23, closer to the opening 22 of the container 21 than the electrical coil 36. The two electrical contacts 27, 29 on second longitudinal section 25 of the wick 23 may again be two metallic jackets which are disposed about the second section of the wick and which are electrically separated and isolated from each other by an intermediate polymeric jacket 28. The electrically operated vaporizer further comprises a susceptor material 31, 32, 33, which is distributed throughout the second longitudinal section 25 of the wick at least within the longitudinal extension of the induction coil 36. In use the induction coil 36 produces an alternating electromagnetic field which induces a heat generating eddy current in the susceptor material 31, 32, 33. The susceptor material 31, 32, 33 is in thermal proximity of the aerosol forming substrate which is transported by the wick 23. The heated susceptor material 31, 32, 33 in turn heats the second longitudinal section 25 of the wick 23 which comprises the aerosol forming substrate which is capable of releasing volatile compounds that can form the aerosol.

Inductive heating is a known phenomenon described by Faraday's law of induction and Ohm's law. More specifically, Faraday's law of induction states that if the magnetic induction in a conductor is changing, a changing electric field is produced in the conductor. Since this electric field is produced in a conductor, a current, known as an eddy current, will flow in the conductor according to Ohm's law. The eddy current will generate heat proportional to the current density and the conductor resistivity. A conductor which is capable of being inductively heated is known as a susceptor material. The present invention employs an induction coil, which is capable of generating an alternating electromagnetic field from an AC source such as an LC circuit. Heat generating eddy currents are produced in the susceptor material which is in thermal proximity to the aerosol-forming substrate which transported by the wick 23 and which is capable of releasing volatile compounds that can form an aerosol upon heating of the aerosol-forming substrate. The primary heat transfer mechanisms from the susceptor material 31, 32, 33 to the aerosol forming substrate are conduction, radiation and possibly convection. The susceptor material may be one of particulate 31, or filament 32, or mesh-like 33 configuration, or mixtures thereof. In FIG. 13, for illustration purposes only, all three configurations are shown. It should be noted though, that the cartridge may also comprise only one or a mixture of the mentioned geometric configurations of susceptors.

Finally it should further be noted, that even a cartridge may be provided, which comprises only susceptor material within the second longitudinal section of the wick. The induction coil on the wick may be omitted. Instead, the induction coil may be integrated into the mouthpiece portion or into the tubular coupling member of the aerosol-generating device. When the cartridge is inserted into the aerosol-generating device, the second longitudinal section of the wick, which comprises the susceptor material, is located within the induction coil, and contactless heating thereof for the production of aerosol may be accomplished.

Figure 8:
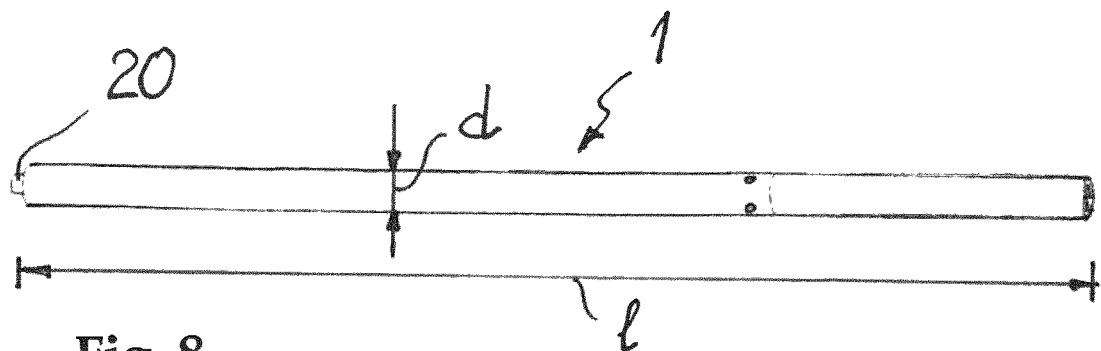
FIG. 8 shows a view of an aerosol-generating device according to FIG. 2 with a cartridge inserted.

In FIG. 8 a handheld aerosol-generating device 1 with an inserted cartridge 20 is shown.

Such a configuration constitutes a handheld aerosol-generating system, which may be ready for use by a customer. The aerosol-generating device 1 has a total axial length of about 80 mm to 110 mm. An outside diameter d of the aerosol-generating device 1 is smaller than 7.5 mm. In a preferred embodiment the outside diameter d of the aerosol-generating device 1 amounts to only about 4 mm to 6 mm.

Figure 9:
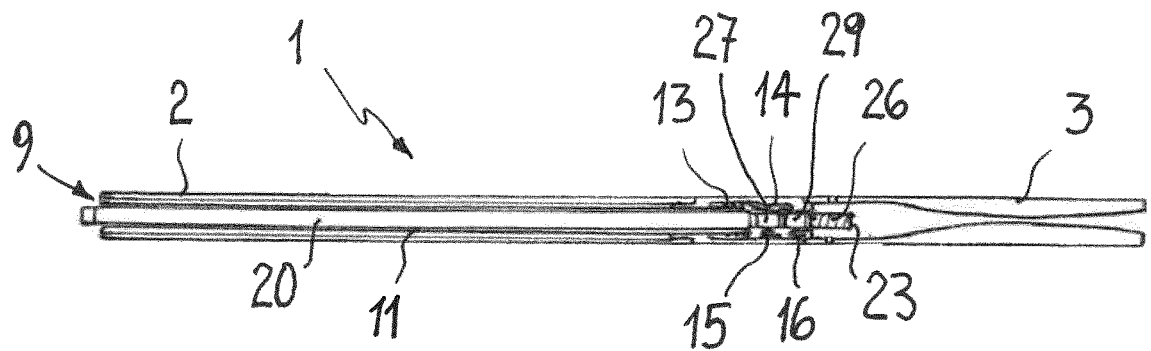
FIG. 9 shows an axially sectioned view of the aerosol-generating device with cartridge of FIG. 8.

FIG. 9 shows an axially sectioned view of the aerosol-generating device 1 with inserted cartridge 20. The aerosol-generating device 1 is configured for an axial insertion of the cartridge 20 through the opening 9 in the elongate tubular member 2. The cartridge 20 is inserted with the wick 23 and the electrical coil 26 in leading position. The tubular coupling member 7 may comprise mechanical locking elements for releasably securing the cartridge 20 in the aerosol-generating device 1. The mechanical locking elements for releasably securing an inserted cartridge may be of the push lock/release type and may comprise a spring 13 and a coupling element 14. When a cartridge 20 is inserted into the elongate receptacle 11 of the elongate tubular component 2 it's leading end bearing the electrical coil 26 pushes against the mechanical locking elements 13, 14 and activates them in order to releasably engage and lock the cartridge 20. By axially pushing the cartridge 20 towards the mouthpiece part 3 the mechanical locking mechanism is activated again and the cartridge 20 may be released. The tubular coupling member 7 further comprises two corresponding electrical contacts 15, 16 which automatically contact the two electrical contacts 27, 29 on the wick 23, when the cartridge 20 is inserted into the elongate receptacle 11. The two corresponding electrical contacts 15, 16 within the tubular coupling member 7 may e.g. be constructed as spring loaded metallic levers or as metallic spring clips.

In case that an embodiment of the aerosol-generating device is provided, in which the elongate tubular component is connected directly with a modified mouthpiece part, the mechanical locking elements for releasably securing the cartridge, and the corresponding mechanical contacts for establishing an electrical connection with the two electrical contacts on the wick of the cartridge, may be provided within the modified mouth piece part. The modification of the mouth piece part then mainly consists in an axially longer build thereof.

Figure 10:
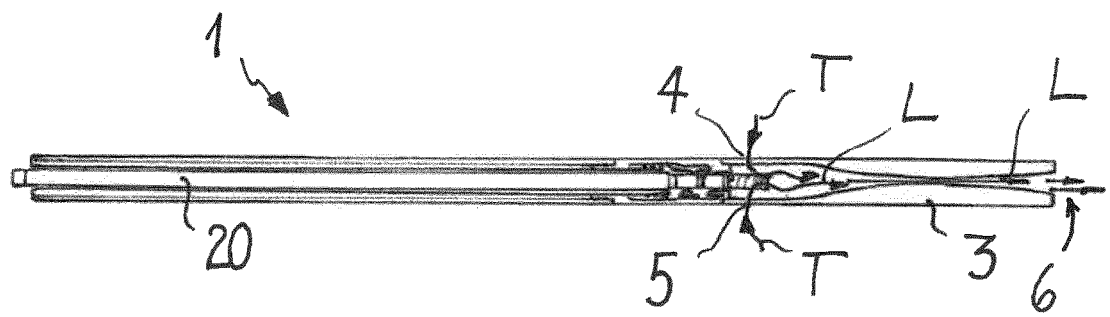
FIG. 10 is a view corresponding to FIG. 9 showing an air flow within the aerosol-generating device.

FIG. 10 again shows and axially sectioned view of the aerosol-generating device 1 with inserted cartridge 20. More specifically the drawing shows the air flow with in the device 1. When the cartridge is fully inserted into the aerosol-generating device 1 and releasably secured therein, the wick 23 of the cartridge bearing the electrical coil 26 is located in immediate vicinity of the air inlets 4, 5 in the mouthpiece portion 3. When a consumer sucks on the mouthpiece portion 3, air enters the device 1 through the air inlets 4, 5, which is indicated by the arrows T. On its path towards the outlet 6 of the mouthpiece portion 3 the air travels about transversal to the portion of the wick 23 which carries the electrical coil and takes up aerosol, which is generated due to the heating of the wick 23. The mixture of air and aerosol then is sucked about longitudinally towards the mouth of the consumer, which is indicated by the arrows L. The generally longitudinal air path inside of the mouthpiece portion 3 may have the shape of a jet nozzle, similar to that of a Lavale nozzle. Due to this shape the air flow including the aerosol is accelerated just prior to entry into the mouth of the consumer.

Figure 11:
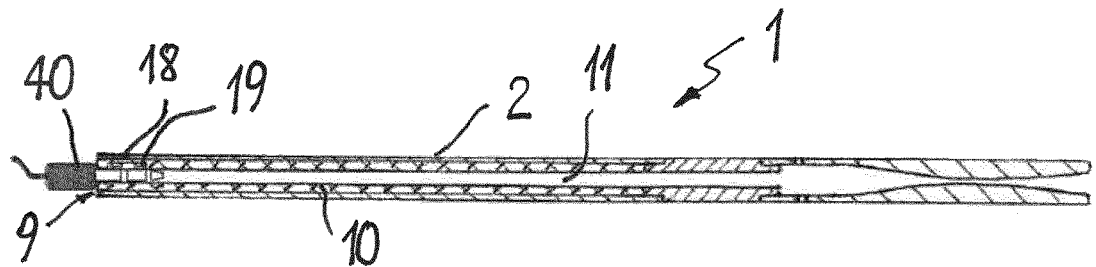
FIG. 11 shows an axially sectioned view of an aerosol-generating device having recharging function.

In FIG. 11 an embodiment of the aerosol-generating device 1 is shown, which is configured to be recharged. For that purpose the annular electric power source 10 within the elongate tubular component 2 may be provided with two electrical recharging contacts 18, 19 which are located near the front end of the elongate tubular component. The electrical recharging contacts 18, 19 may be provided such that they face the elongate receptacle 11 for the cartridge. They may, e.g. be constructed as spring loaded metallic levers or as metallic spring clips. With the cartridge removed, a two terminal mini jack 40 may be inserted into the opening 9 at the front end of the elongate tubular component 2 to provide electrical contact with the two electrical recharging contacts 18, 19. The two terminal mini jack 40 may e.g. be constructed similar to a mini jack commonly used for headphones or the like. With this construction a recharging of the annular electrical power source 10 may be accomplished without any disassembly of the aerosol-generating device 1.

Figure 12:
FIG. 12 shows a view of an aerosol-generating device according to FIG. 11 during recharging.

FIG. 12 shows a view of a handheld aerosol-generating device during recharging. The two terminal mini jack 40 is inserted into the elongate receptacle in the elongate tubular component. The recharging contacts are not visible from outside. The connectivity solution for charging of the electric power source inside the elongate tubular component enables a direct connection without any disassembly of any part of the device 1. It is highly reliable and does not interfere with the cartridge in the normal usage. Rather, the recharging contacts might even be used to provide electrical contact in between the electric power source and additional contacts on the cartridge, e.g. for powering a LED on a trailing end of the cartridge.

The handheld aerosol-generating device according to the invention is of a very slim and light build. Its appearance is very elegant and appealing, and matches the customers' requirement for a sophisticated premium product.

While different embodiments of the invention have been described with reference to the accompanying drawings, the invention is not limited to these embodiments. Various changes and modifications are conceivable without departing from the overall teaching of the present invention. Therefore, the scope of protection is defined by the appended claims.

The invention claimed is:

1. A handheld aerosol-generating device comprising an elongate tubular component having an axial length and accommodating an electric power source, and a mouthpiece portion having at least one air inlet and an outlet communicating with one another, which mouthpiece is detachably connected with the elongate tubular component, wherein the electric power source is of an annular configuration extending at least about a major part of the axial length of the tubular component, and encloses an elongate receptacle which is open towards the mouthpiece portion, for accommodation of a cartridge comprising a supply of aerosol-forming substrate and an electrically operated vaporizer, wherein the elongate tubular component is open on a front end opposite a longitudinal end facing towards the mouthpiece to allow the insertion of the cartridge from the front end.

2. The handheld aerosol-generating device according to claim 1, wherein the electric power source is one of a battery or an accumulator.

3. The handheld aerosol-generating device according to claim 2, wherein the battery or accumulator is constructed based on one of Lithium sulphur chemistry, or on hyper-capacitor chemistry elements.

4. The handheld aerosol-generating device according to claim 3, wherein the battery is based on hyper-capacitor chemistry elements and comprises cobalt oxide in nanocarbon structures or nickel hydroxide in graphene/porous graphene structures.

5. The handheld aerosol-generating device according to claim 1, wherein the elongate tubular component is open on a front end opposite a longitudinal end facing towards the mouthpiece and wherein the annular electrical power source is provided with electrical recharging contacts which are located near the front end of the elongate tubular component and facing the elongate receptacle for interaction with a two terminal mini jack which may be received in the front end of the elongate tubular component.

6. The handheld aerosol-generating device according to claim 1, wherein the elongate tubular component and the mouthpiece portion are detachably connected by a tubular coupling member, comprising mechanical holding elements for releasably securing a cartridge and mechanical contacts for establishing an electrical connection with the electrically operated vaporizer.

7. The handheld aerosol-generating device according to claim 6, wherein the elongate tubular component, the tubular coupling member, and the mouthpiece portion are enclosed with the flexible casing.

8. A handheld aerosol-generating device, according to claim 1 wherein, the elongate tubular component and the mouthpiece portion are detachably connected by a tubular coupling member, comprising mechanical holding elements for releasably securing a cartridge comprising a supply of aerosol-forming substrate and an electrically operated vaporizer, and mechanical contacts for establishing an electrical connection with corresponding contacts of the electrically operated vaporizer on the cartridge.

9. The handheld aerosol-generating device according to claim 8, wherein the mechanical holding elements are elements of a push lock/release mechanism comprising a spring and a coupling element.

10. The handheld aerosol-generating device according to claim 8, wherein the mechanical holding elements are elements of a frictional holding system and comprise at least one O-ring.

11. The handheld aerosol-generating device according to claim 8, wherein the elongate tubular component is open on a front end opposite a longitudinal end facing towards the tubular coupling member and is adapted for receiving the cartridge from its open front end, with the electrically operated vaporizer protruding from a leading longitudinal end of the cartridge.

12. The handheld aerosol-generating device according to claim 11, wherein the electric power source is provided with first electrical contacts which are located near the front end of the elongate tubular component and facing an elongate receptacle for the cartridge for interaction with corresponding second electrical contacts near a trailing end portion of the cartridge which may be received in the elongate receptacle, which second contacts are electrically connected with an LED which is attached to the trailing end of the cartridge.

13. The handheld aerosol-generating device according to claim 1, further including a control electronics including a puff sensor and a power management of the device, which control electronics may be provided at one of the elongate tubular component, a tubular coupling member, and the mouthpiece portion.

14. The handheld aerosol-generating device according to claim 13, wherein the control electronics is provided as printed circuitry on polymeric film.

15. The handheld aerosol-generating device according to claim 1, wherein the elongate tubular component and a tubular coupling member are made of metals, alloys, plastics, or composite materials containing one or more of those materials, or thermoplastics, such as, e.g., PET, HDPE, PP, PEEK, PS, PVC, PEN, copolymers of the mentioned plastics, bio-plastics, such as, e.g., PLA or PEF, filled plastics and mixtures of the mentioned plastics.

16. The handheld aerosol-generating device according to claim 1, having an outside diameter of from 5 mm to 8 mm.

17. The handheld aerosol-generating device according to claim 16, having an axial length of 80 mm to 110 mm.

18. The handheld aerosol-generating device according to claim 1, wherein the elongate tubular component has an internal diameter of from 2 mm to 2.6 mm.

19. The handheld aerosol-generating device according to claim 1, wherein the elongate tubular component and the mouthpiece portion are enclosed with a flexible casing made of a laminated auto-adhesive paper foil.

20. The handheld aerosol-generating device according to claim 1 and a cartridge for use therein comprising
a tubular container for holding a liquid aerosol-forming substrate, the tubular container having an opening;
an elongate, cylindrical wick having a first longitudinal section which extends into the container, and a second longitudinal section which extends axially beyond the opening of the container; and
at least one of the components of an electrically operated vaporizer which is located at the second longitudinal section of the wick.

21. The handheld aerosol-generating device and the cartridge for use therein according to claim 20, wherein all of the components of the electrically operated vaporizer are located at the second longitudinal section of the wick and include an electrical coil which is wound at least around a part of the second longitudinal section of the wick, the electrical coil having two ends which are connected with two electrical contacts that are located on the second longitudinal section of the wick, closer to the opening of the container than the electrical coil.

22. The handheld aerosol-generating device and the cartridge for use therein according to claim 21, wherein the two electrical contacts are two metallic jackets which are disposed about the second longitudinal section of the wick and are electrically separated and isolated from each other by an intermediate polymeric jacket.

23. The handheld aerosol-generating device and the cartridge for use therein according to claim 21, wherein the electrical coil is a resistance heating coil.

24. The handheld aerosol-generating device and the cartridge for use therein according to claim 21, wherein the electrical coil is an induction coil and wherein the second longitudinal section of the wick, at least within the longitudinal extension of the induction coil comprises a susceptor material.

25. The handheld aerosol-generating device and the cartridge for use therein according to claim 20, wherein the at least one component of the electrically operated vaporizer comprises a susceptor material.

26. The handheld aerosol-generating device and the cartridge for use therein according to claim 24, wherein the susceptor material is one of particulate, or filament, or mesh-like configuration.

27. The handheld aerosol-generating device and the cartridge for use therein according to claim 20, wherein the tubular container is flexible.

28. The handheld aerosol-generating device and the cartridge for use therein according to claim 20, wherein the tubular container at a longitudinal end portion opposite the opening is provided with two electrical contacts which are electrically connected with a LED which is attached to the longitudinal end of the container opposite the opening.

29. The handheld aerosol-generating device and the cartridge for use therein according to claim 20, wherein the cylindrical wick is made of a capillary material.

30. The handheld aerosol-generating device and the cartridge for use therein according to claim 20 wherein the electrically operated vaporizer comprises an induction coil, which is located within the mouthpiece portion or the tubular coupling member.

* * * * *